United States Patent
Voll

(10) Patent No.: US 11,970,596 B2
(45) Date of Patent: Apr. 30, 2024

(54) PHOTOPOLYMERIZABLE COMPOSITIONS AND REACTION PRODUCTS THEREOF

(71) Applicant: 3M INNOVATIVE PROPERTIES COMPANY, St. Paul, MN (US)

(72) Inventor: Constantin-Christian A. Voll, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 18/027,739

(22) PCT Filed: Aug. 10, 2021

(86) PCT No.: PCT/IB2021/057386
§ 371 (c)(1),
(2) Date: Mar. 23, 2023

(87) PCT Pub. No.: WO2022/064292
PCT Pub. Date: Mar. 31, 2022

(65) Prior Publication Data
US 2023/0391985 A1 Dec. 7, 2023

Related U.S. Application Data

(60) Provisional application No. 63/083,462, filed on Sep. 25, 2020.

(51) Int. Cl.
*C08K 5/45* (2006.01)
*C07D 335/16* (2006.01)

(52) U.S. Cl.
CPC .............. *C08K 5/45* (2013.01); *C07D 335/16* (2013.01)

(58) Field of Classification Search
CPC ................................ C07D 335/16; C08K 5/45
See application file for complete search history.

(56) References Cited

U.S. PATENT DOCUMENTS

| | | | |
|---|---|---|---|
| 3,729,313 A | 4/1973 | Smith | |
| 3,741,769 A | 6/1973 | Smith | |
| 3,808,006 A | 4/1974 | Smith | |
| 4,250,053 A | 2/1981 | Smith | |
| 4,356,296 A | 10/1982 | Griffith et al. | |
| 4,394,403 A | 7/1983 | Smith | |
| 4,642,126 A | 2/1987 | Zador et al. | |
| 4,648,843 A | 3/1987 | Mitra | |
| 4,652,274 A | 3/1987 | Boettcher et al. | |
| 5,076,844 A | 12/1991 | Fock et al. | |
| 5,545,676 A | 8/1996 | Palazzotto et al. | |
| 8,883,873 B2 * | 11/2014 | Loccufier | C08F 299/065 525/132 |
| 2020/0282638 A1 | 9/2020 | Holt et al. | |

FOREIGN PATENT DOCUMENTS

| | | |
|---|---|---|
| EP | 0201778 B1 | 12/1988 |
| EP | 0201031 B1 | 8/1989 |
| EP | 0373384 B1 | 10/1992 |
| WO | 2000038619 A2 | 7/2000 |
| WO | 2000042092 A1 | 7/2000 |
| WO | 2001007444 A1 | 2/2001 |
| WO | 2001092271 A1 | 12/2001 |
| WO | 2011103878 A1 | 9/2011 |

OTHER PUBLICATIONS

Bouzrati-Zerelli, "A novel class of photoinitiators with a thermally activated delayed fluorescence (TADF) property", New Journal of Chemistry, May 2018, vol. 42, No. 10, pp. 8261-8270.
He, "Polymorphism dependent triplet-involved emissions of a pure organic luminogen", Chinese Chemical Letters, Apr. 2019, vol. 30, No. 4, pp. 933-936.
Hola, "Thioxanthone Derivatives as a New Class of Organic Photocatalysts for Photopolymerisation Processes and the 3D Printing of Photocurable Resins under Visible Light", Catalysts, Aug. 2020, vol. 10, No. 8, Article 903, 27 pages.
International Search Report for PCT International Application No. PCT/IB2021/057386, dated Feb. 11, 2022, 5 pages.
Mousawi, "Carbazole Derivatives with Thermally Activated Delayed Fluorescence Property as Photoinitiators/Photoredox Catalysts for LED 3D Printing Technology", Macromolecules, Jul. 2017, Vo. 50, No. 13, pp. 4913-4926.
Wang, "Structure-Performance Investigation of Thioxanthone Derivatives for Developing Color Tunable Highly Efficient Thermally Activated Delayed Fluorescence Emitters", ACS Applied Materials & Interfaces, Apr. 2016, vol. 8, vol. 13, pp. 8627-8636.
Wang, "Synthesis of "donor-bridge-acceptor" triad compounds containing the aromatic sulfer bridges", Dyes and Pigments, Jan. 2000, vol. 44, No. 2, pp. 93-100.

(Continued)

*Primary Examiner* — Vickey Nerangis

(57) ABSTRACT

Polymerizable compositions comprise at least one free-radically or cationically polymerizable compound; and a photoinitiator system, wherein the photoinitiator system comprises a compound represented by the formula: (I) wherein: each $R^1$ independently represents an alkyl group having from 1 to 6 carbon atoms, and each $R^2$ independently represents H, an alkyl group having from 1 to 4 carbon atoms, an alkoxy group having from 1 to 4 carbon atoms, F, Cl, or Br. Polymerized reaction products are also disclosed.

12 Claims, No Drawings

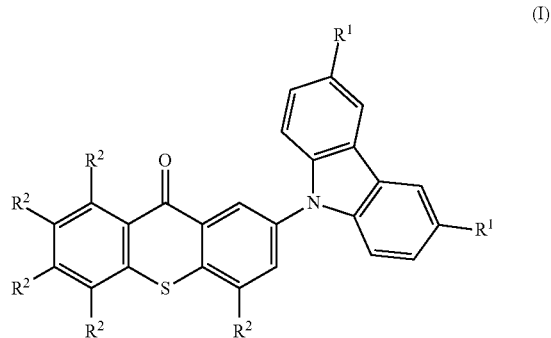

(I)

(56) References Cited

OTHER PUBLICATIONS

Zhang, "Sterically shielded blue thermally activated delayed fluorescence emitters with improved efficiency and stability", Materials Horizons, Mar. 2016, vol. 3, No. 2, pp. 145-151.

* cited by examiner

PHOTOPOLYMERIZABLE COMPOSITIONS AND REACTION PRODUCTS THEREOF

CROSS REFERENCE TO RELATED APPLICATIONS

This application is a national stage filing under 35 U.S.C. 371 of PCT/IB2021/057386, filed Aug. 10, 2021, which claims the benefit of Provisional Application No. 63/083,462, filed Sep. 25, 2020, the disclosure of which is incorporated by reference in its/their entirety herein.

TECHNICAL FIELD

The present disclosure broadly relates to photopolymerizable compositions and their cured reaction products.

BACKGROUND

Photopolymerization of monomers is widely practiced in the manufacture of polymers, and especially thin polymer coatings. Various types of photoinitiator systems are known including, for example, Type I photoinitiators that function by unimolecular decomposition, Type II photoinitiator systems typically based on intermolecular H-atom abstraction, and redox photoinitiator systems based on intermolecular electron transfer.

However, the sheer number of commercially available photoinitiator systems indicates that no one-size-fits all solution has been found to date.

SUMMARY

There is a continuing need for new useful photoinitiators for photoinitiators of free-radical polymerization.

It is presently discovered that certain compounds are useful as photoinitiators for free-radical polymerization that have efficiencies in excess of widely used photoinitiators such a thioxanthone and 2-chlorothioxanthen-9-one (often referred to in the art simply as chlorothioxanthone or CTX). They are useful for photoinitiating and/or photocatalyzing cationic polymerization when combined with certain onium salt compounds.

In one aspect, the present disclosure provides a polymerizable composition comprising:
at least one free-radically polymerizable compound; and
a photoinitiator system, wherein the photoinitiator system comprises a compound represented by the formula:

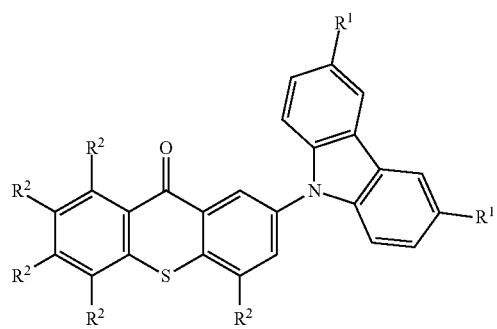

wherein:
each $R^1$ independently represents an alkyl group having from 1 to 6 carbon atoms, and
each $R^2$ independently represents H, an alkyl group having from 1 to 4 carbon atoms, an alkoxy group having from 1 to 4 carbon atoms, F, Cl, or Br.

In another aspect, the present disclosure provides a polymerizable composition comprising:
at least one cationically polymerizable compound; and
a photoinitiator system, wherein the photoinitiator system comprises:
a diaryliodonium salt; and
a compound represented by the formula:

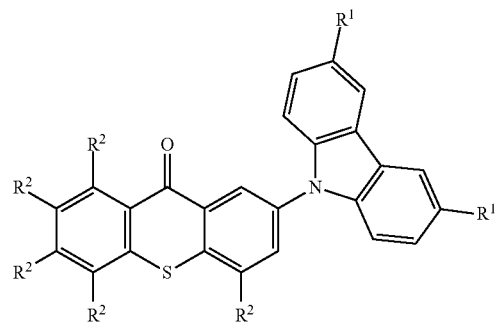

wherein:
each $R^1$ independently represents an alkyl group having from 1 to 6 carbon atoms, and
each $R^2$ independently represents H, an alkyl group having from 1 to 4 carbon atoms, an alkoxy group having from 1 to 4 carbon atoms, F, Cl, or Br.

In another aspect, the present disclosure provides a polymerized reaction product of either of the aforementioned polymerizable compositions.

As used herein, the prefix "(meth)acryl" refers to acryl and/or methacryl. For example, (meth)acrylate refers to acrylate and/or methacrylate.

Features and advantages of the present disclosure will be further understood upon consideration of the detailed description as well as the appended claims.

DETAILED DESCRIPTION

In some embodiments, polymerizable compositions according to the present disclosure are free-radically polymerizable. Such compositions comprise at least one (e.g., 1, 2, 3, 4, 5, or more) free-radically polymerizable compounds such a monomers oligomers, and polymers having at least one (e.g., 1, 2, 3, 4, 5, 6, or more) terminal and/or pendant free-radically polymerizable group(s).

Exemplary free-radically polymerizable compounds include (meth)acrylates, (meth)acrylamides, N-vinyl compounds, vinyl ethers, vinyl esters, other vinyl compounds, and combinations thereof. Useful free-radically polymerizable compounds may comprise an ethylenically-unsaturated compound having one or more (e.g., one, two, three, four, or more) free-radically polymerizable groups.

Examples of suitable (meth)acrylates and (meth)acrylamides include mono-, di-, and poly-(meth)acrylates and (meth)acrylamides such as, for example, 1,2,4-butanetriol tri(meth)acrylate, 1,3-butylene glycol di(meth)acrylate, 1,3-propanediol di(meth)acrylate, 1,4-butanediol di(meth)acrylate, 1,4-cyclohexanediol di(meth)acrylate, 1,6-hexanediol di(meth)acrylate, 1,6-hexanediol monomethacrylate monoacrylate, 2-phenoxyethyl (meth)acrylate, alkoxylated cyclohexanedimethanol di(meth)acrylates, alkoxylated hexanediol di(meth)acrylate, alkoxylated neopentyl glycol di(meth)acrylate, allyl (meth)acrylate, bis[1-(2-(meth)acryloxy)]-p-ethoxyphenyldimethylmethane, bis[1-(3-(meth)acryloxy-2-hydroxy)]-p-propoxyphenyldimethylmethane, caprolactone modified dipentaerythritol hexa(meth)acrylate, caprolactone modified neopentyl glycol hydroxypivalate di(meth)acrylate, cyclohexanedimethanol di(meth)acrylate, diethylene glycol di(meth)acrylate, dipentaerythritol penta(meth)acrylate, dipropylene glycol di(meth)acrylate, di-trimethylolpropane tetra(meth)acrylate, ethoxylated (10) bisphenol A di(meth)acrylate, ethoxylated (20) trimethylolpropane tri(meth)acrylate, ethoxylated (3) bisphenol A di(meth)acrylate, ethoxylated (3) trimethylolpropane tri(meth)acrylate, ethoxylated (30) bisphenol A di(meth)acrylate, ethoxylated (4) bisphenol A di(meth)acrylate, ethoxylated (4) pentaerythritol tetra(meth)acrylate, ethoxylated (6) trimethylolpropane tri(meth)acrylate, ethoxylated (9) trimethylolpropane tri(meth)acrylate, ethoxylated bisphenol A di(meth)acrylate, ethyl (meth)acrylate, ethylene glycol di(meth)acrylate, 2-ethylhexyl (meth)acrylate, glycerol tri(meth)acrylate, hydroxypivalaldehyde modified trimethylolpropane di(meth)acrylate, isobornyl (meth)acrylate, isopropyl (meth)acrylate, methyl (meth)acrylate, neopentyl glycol di(meth)acrylate, n-hexyl (meth)acrylate, pentaerythritol tetra(meth)acrylate, pentaerythritol tri(meth)acrylate, polyethylene glycol (200) di(meth)acrylate, polyethylene glycol (400) di(meth)acrylate, polyethylene glycol (600) di(meth)acrylate, propoxylated (3) glyceryl tri(meth)acrylate, propoxylated (3) trimethylolpropane tri(meth)acrylate, propoxylated (5.5) glyceryl tri(meth)acrylate, propoxylated (6) trimethylolpropane tri(meth)acrylate), propoxylated neopentyl glycol di(meth)acrylate, sorbitol hexa(meth)acrylate, stearyl (meth)acrylate, tetraethylene glycol di(meth)acrylate, tetrahydrofurfuryl (meth)acrylate, tricyclodecane-dimethanol di(meth)acrylate, triethylene glycol di(meth)acrylate, trimethylolpropane tri(meth)acrylate, tripropylene glycol di(meth)acrylate, tris(2-hydroxyethyl)isocyanurate tri(meth)acrylate, urethane (meth)acrylates, polyester (meth)acrylates, epoxy (meth)acrylates, methylene bis-acrylamide, methylene bis-methacrylamide, 1,6-hexamethylene bis-acrylamide, diethylene triamine tris-acrylamide and β-methacrylaminoethylmethacrylate; copolymerizable mixtures of (meth)acrylated monomers such as those in U.S. Pat. No. 4,652,274 (Boettcher et al.), (meth)acrylated oligomers such as those of U.S. Pat. No. 4,642,126 (Zador et al.), and poly(ethylenically-unsaturated) carbamoyl isocyanurates such as those disclosed in U.S. Pat. No. 4,648,843 (Mitra).

Suitable free-radically polymerizable compounds also include (meth)acrylamides such as, for example, N,N-dimethylacrylamide and methylene bis(meth)acrylamide, and diacetone (meth)aciylamide.

Suitable free-radically polymerizable compounds also include N-vinylamides (including lactams) such as, for example, N-vinylformamide, N-vinylacetamide, N-vinylpyrrolidone, and N-vinylcaprolactam.

Examples of suitable free-radically polymerizable vinyl compounds also include styrene, diallyl phthalate, divinyl succinate, divinyl adipate, and divinyl phthalate. Other suitable free-radically polymerizable compounds include siloxane-functional (meth)acrylates as disclosed, for example, in PCT Publications, WO 00/38619 (Guggenberger et al.), WO 01/92271 (Weinmann et al.), WO 01/07444 (Guggenberger et al.), WO 00/42092 (Guggenberger et al.), and fluoropolymer-functional (meth)acrylates as disclosed, for example, in U.S. Pat. Nos. 5,076,844 (Fock et al.), 4,356,296 (Griffith et al.), EP 0 373 384 (Wagenknecht et al.), EP 0 201 031 (Reiners et al.), and EP 0 201 778 (Reiners et al.).

Suitable free-radically polymerizable compounds may contain hydroxyl groups and free-radically active functional groups in a single molecule. Examples of such materials include hydroxyalkyl (meth)acrylates such as 2-hydroxyethyl (meth)acrylate and 2-hydroxypropyl (meth)acrylate, glycerol mono- or di-(meth)acrylate, trimethylolpropane mono- or di-(meth)acrylate, pentaerythritol mono-, di-, and tri-(meth)acrylate, sorbitol mono-, di-, tri-, tetra-, or penta-(meth)acrylate, and 2,2-bis[4-(2-hydroxy-3-methacryloxypropoxy)phenyl]-propane (bisGMA).

Suitable free-radically polymerizable compounds also include vinyl ethers and vinyl esters. Exemplary vinyl ethers include, ethyl vinyl ether, propyl vinyl ether, isobutyl vinyl ether, cyclohexyl vinyl ether, 2-ethylhexyl vinyl ether, butyl vinyl ether, ethylene glycol monovinyl ether, diethylene glycol divinyl ether, butanediol divinyl ether, hexanediol divinyl ether, cyclohexanedimethanol monovinyl ether, and 1,4-cyclohexanedimethanol divinyl ether. Exemplary vinyl esters include, Exemplary vinyl esters include vinyl acetate, vinyl propionate, vinyl butyrate, vinyl caprylate, and vinyl benzoate.

Suitable free-radically polymerizable compounds are available from a wide variety of commercial sources such as, for example, Sartomer Co., Exton, Pennsylvania, or can be made by known methods.

Typically, the curable composition includes a sufficient quantity of free-radically polymerizable compound(s) to provide a desired setting or hardening rate and desired overall properties following curing/hardening. Mixtures of free-radically polymerizable compounds can be used if desired.

Photoinitiator systems useful in practice of the present disclosure includes at least one compound represented by Formula I, below:

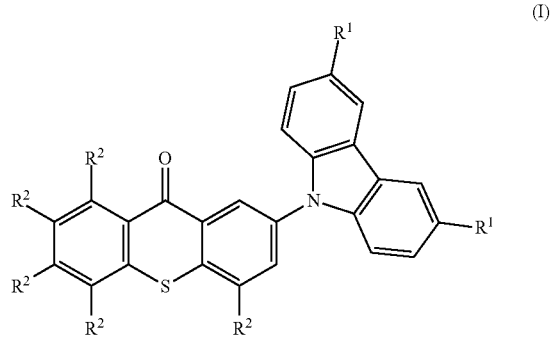

(I)

In Formula 1, each $R^1$ independently represents an alkyl group having from 1 to 6 carbon atoms. Examples of $R^1$ include methyl, ethyl, n-propyl, isopropyl, n-butyl, isobutyl, tert-butyl, n-pentyl, n-hexyl, and isohexyl.

Each $R^2$ independently represents H, an alkyl group having from 1 to 4 carbon atoms, an alkoxy group having from 1 to 4 carbon atoms, F, Cl, or Br. Examples of $R^2$ include H, methyl, ethyl, n-propyl, isopropyl, n-butyl, sec-butyl, and tert-butyl, methoxy, ethoxy, n-propoxy, isopropoxy, n-butoxy, sec-butoxy, and tert-butoxy, F, Cl, and Br. In some embodiments, 1, 2, 3, 4, 5 of groups $R^2$ are H.

Compounds according to Formula I can be prepared, for example, by a palladium-catalyzed N-arylation of a corresponding carbazole with a corresponding chlorothioxanthone, for example, generally according to the procedure set forth in the synthesis of 2-(9H-carbazol-9-yl)-9H-thioxanthen-9-one in the Examples.

The photoinitiator system may be present in any amount, but typically less than 10 percent by weight, more preferably less than 5 percent by weight, and more preferably less than 3 percent by weight, based on the total weight of the polymerizable composition.

In some embodiments, polymerizable compositions according to the present disclosure are photocationically polymerizable (i.e., initiated by actinic electromagnetic radiation to cause cationic polymerization). Such compositions comprise at least one (e.g., 1, 2, 3, 4, 5, or more) cationically polymerizable compounds such a monomers oligomers, and polymers having at least one (e.g., 1, 2, 3, 4, 5, 6, or more) terminal and/or pendant cationically polymerizable group(s).

Exemplary cationically polymerizable compounds include vinyl esters, vinyl esters, epoxy group-containing compounds, and combinations thereof. Useful cationically polymerizable compounds may comprise an ethylenically-unsaturated compound having one or more (e.g., one, two, three, four, or more) cationically polymerizable groups.

Exemplary cationically polymerizable compounds include epoxy compounds, oxetane compounds, cyclic lactone compounds, cyclic acetal compounds, cyclic thioether compounds, spiro-orthoester compounds, vinyl ether, vinyl esters, and other vinyl compounds.

Examples of epoxy compounds include, for example, alicyclic epoxy compounds, aromatic epoxy compounds, and aliphatic epoxy compounds.

Specific examples of the alicyclic epoxy compounds include polyglycidyl ethers of polyhydric alcohols having at least one alicyclic ring; and cyclohexene oxide or cyclopentene oxide-containing compounds obtained by epoxidizing a cyclohexene ring or cyclopentene ring-containing compound with an oxidizing agent. Examples of these compounds include hydrogenated bisphenol-A diglycidyl ether, 3,4-epoxycyclohexylmethyl-3,4-epoxycyclohexane carboxylate, 3,4-epoxy-1-methylcyclohexyl-3,4-epoxy-1-methylcyclohexane carboxylate, 6-methyl-3,4-epoxycyclohexylmethyl-6-methyl-3,4-epoxycyclohexane carboxylate, 3,4-epoxy-3-methylcyclohexylmethyl-3,4-epoxy-3-methylcyclohexane carboxylate, 3,4-epoxy-5-methylcyclohexylm-ethyl-3,4-epoxy-5-methylcyclohexane carboxylate, 2-(3,4-epoxycyclohexyl-5,5-spiro-3,4-epoxy)cyclohexane-metadioane, bis(3,4-epoxycyclohexylmethyl)adipate, 3,4-epoxy-6-methylcyclohexyl carboxylate, methylenebis(3,4-epoxycyclohexane), dicyclopentadiene diepoxide, ethylenebis(3,4-epoxycyclohexanecarboxylate), dioctyl epoxyhexahydrophthalate, and di-2-ethylhexyl epoxyhexahydrophthalate.

Examples of aromatic epoxy compounds include polyglycidyl ethers of polyhydric phenols having at least one aromatic ring or alkylene oxide adducts thereof, such as glycidyl ethers of bisphenol A, bisphenol F or an alkylene oxide adduct thereof; and epoxy novolac resins.

Examples of aliphatic epoxy compounds include polyglycidyl ethers of aliphatic polyhydric alcohols or alkylene oxide adducts thereof; polyglycidyl esters of aliphatic long-chain polybasic acids; homopolymers synthesized by vinyl polymerization of glycidyl acrylate or glycidyl methacrylate; and copolymers synthesized by vinyl polymerization of glycidyl acrylate or glycidyl methacrylate and other vinyl monomer(s). Representative examples of these compounds include glycidyl ethers of polyhydric alcohols, such as 1,4-butanediol diglycidyl ether, 1,6-hexanediol diglycidyl ether, glycerol triglycidyl ether, trimethylolpropane triglycidyl ether, sorbitol tetraglycidyl ether, dipentaerythritol hexaglycidyl ether, polyethylene glycol diglycidyl ether and polypropylene glycol diglycidyl ether; polyglycidyl ethers of polyether polyols obtained by addition of one or more alkylene oxides to an aliphatic polyhydric alcohol, such as propylene glycol, trimethylolpropane and glycerin; and diglycidyl esters of aliphatic long-chain dibasic acids. Examples thereof also include monoglycidyl ethers of aliphatic higher alcohols; monoglycidyl ethers of phenol, cresol, butylphenol, or polyether alcohols obtained by addition of an alkylene oxide thereto; glycidyl esters of higher fatty acids; epoxidized soybean oil; octyl epoxystearate; butyl epoxystearate; and epoxidized polybutadienes.

Examples of oxetane compounds include 3-ethyl-3-hydroxymethyloxetane, 3-(meth)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl (3-ethyl-3-oxetanylmethyl) ether, isobornyloxyethyl (3-ethyl-3-oxetanylmethyl) ether, isobornyl (3-ethyl-3-oxetanylmethyl) ether, 2-ethylhexyl (3-ethyl-3-oxetanylmethyl) ether, ethyl diethylene glycol (3-ethyl-3-oxetanylmethyl) ether, dicyclopentadiene (3-ethyl-3-oxetanylmethyl) ether, dicyclopentenyloxyethyl (3-ethyl-3-oxetanylmethyl) ether, dicyclopentenyl (3-ethyl-3-oxetanylmethyl) ether, tetrahydrofurfuryl (3-ethyl-3-oxetanylmethyl) ether, tetrabromophenyl (3-ethyl-3-oxetanylmethyl) ether, 2-tetrabromophenoxyethyl (3-ethyl-3-oxetanylmethyl) ether, tribromophenyl (3-ethyl-3-oxetanylmethyl) ether, 2-tribromophenoxyethyl (3-ethyl-3-oxetanylmethyl) ether, 2-hydroxyethyl (3-ethyl-3-oxetanylmethyl) ether, 2-hydroxypropyl (3-ethyl-3-oxetanylmethyl) ether, butoxyethyl (3-ethyl-3-oxetanylmethyl) ether, pentachlorophenyl (3-ethyl-3-oxetanylmethyl) ether, pentabromophenyl (3-ethyl-3-oxetanylmethyl) ether, bornyl (3-ethyl-3-oxetanylmethyl) ether, 3,7-bis(3-oxetanyl)-5-oxa-nonan, 3,3'-(1,3-(2-methylenyl)propanediyl-bis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol-bis(3-ethyl-3-oxetanylmethyl) ether, dicyclopentenyl-bis(3-ethyl-3-oxetanylmethyl) ether, triethylene glycol-bis(3-ethyl-3-oxetanylmethyl) ether, tetraethylene glycol-bis(3-ethyl-3-oxetanylmethyl) ether, tricyclodecane-diyldimethylene (3-ethyl-3-oxetanylmethyl) ether, trimethylolpropane tris(3-ethyl-3-oxetanylmethyl) ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl) ether, pentaerythritol tetrakis(3-ethyl-3-oxetanylmethyl) ether, polyethylene glycol-bis(3-ethyl-3-oxetanylmethyl) ether, dipentaerythritol hexakis(3-ethyl-3-oxetanylmethyl) ether, dipentaerythritol pentakis(3-ethyl-3-oxetanylmethyl) ether, dipentaerythritol tetrakis(3-ethyl-3-oxetanylmethyl) ether, caprolactone-modified dipentaerythritol hexakis(3-ethyl-3-oxetanylmethyl) ether, caprolactone-modified dipentaerythritol pentakis(3-ethyl-3-oxetanylmethyl) ether, ditrimethylolpropane tetrakis(3-ethyl-3-oxetanylmethyl) ether, EO-modified bisphenol-A bis (3-ethyl-3-oxetanylmethyl) ether, PO-modified bisphenol-A bis(3-ethyl-3-oxetanylmethyl) ether, EO-modified hydrogenated bisphenol-A bis(3-ethyl-3-oxetanylmethyl) ether, PO-modified hydrogenated bisphenol-A bis(3-ethyl-3-oxetanylmethyl) ether, and EO-modified bisphenol-F (3-ethyl-3-oxetanylmethyl) ether.

Examples of other cationically polymerizable compounds include cyclic lactone compounds such as β-propiolactone, and ε-caprolactone; cyclic acetal compounds such as trioxane, 1,3-dioxolane, and 1,3,6-trioxanecyclooctane; cyclic thioether compounds such as tetrahydrothiophene derivatives; spiro-orthoester compounds obtained by reaction between any of the above-described epoxy compounds and lactone; vinyl ether compounds such as vinyl ether, propyl vinyl ether, isobutyl vinyl ether, cyclohexyl vinyl ether, 2-ethylhexyl vinyl ether, butyl vinyl ether, ethylene glycol monovinyl ether, diethylene glycol divinyl ether, butanediol divinyl ether, hexanediol divinyl ether, cyclohexanedimethanol monovinyl ether, and 1,4-cyclohexanedimethanol divinyl ether, and the propenyl ether of propylene glycol; vinyl esters such as vinyl acetate, vinyl propionate, vinyl butyrate, vinyl caprylate, and vinyl benzoate; vinyl compounds such as ethylenically unsaturated compounds, including styrene, vinylcyclohexene, isobutylene and polybutadiene; oxolane compounds such as tetrahydrofuran and 2,3-dimethyltetrahydrofuran; thiirane compounds such as ethylene sulfide and thioepichlorohydrin; thietane compounds such as 1,3-propyne sulfide, and 3,3-dimethylthietane.

Polymerizable compositions of the present disclosure may contain a wide variety of adjuvants depending upon the desired end use. Suitable adjuvants may include solvents, diluents, resins, binders, plasticizers, pigments, dyes, inorganic or organic reinforcing or extending fillers (at preferred amounts of about 10% to about 90% by weight, based on the total weight of the composition), thixotropic agents, indicators, inhibitors, stabilizers, UV absorbers, medicaments (e.g., leachable fluorides) and the like. The amounts and types of such adjuvants, and their manner of addition to a composition of the invention will be familiar to those skilled in the art.

Photoinitiator systems useful in practice of the present disclosure may consist of one or more compounds represented by Formula I, but in many cases, they advantageously further comprise at least one of an electron donor and/or an electron acceptor. The electron is transferred to or from an excited of the compound of Formula I after absorption of electromagnetic radiation.

Useful electron acceptors are preferably decomposed when reduced by one electron. Examples include diaryliodonium salts, triarylsulfonium salts, triarylsulfoxonium salts, and trihalomethyltriazines that are soluble in the polymerizable composition. Examples may include the abovementioned diaryliodonium and/or triarylsulfonium salts with Cl$^-$, Br$^-$, I$^-$; however, satisfactory solubility in organic mixtures is often achieved using complex counterions such as BF$_4^-$, PF$_6^-$, AsF$_6^-$, SbF$_6^-$, and/or Sb(OH)F$_5^-$. The counterion should be selected such that it does not interfere to an appreciable extent with the desired polymerization process. In the case, of free-radical polymerization many counterions are suitable, but in the case of cationic polymerizable, good results are often obtained using BF$_4^-$, PF$_6^-$, SbF$_6^-$, and/or Sb(OH)F$_5^-$.

Mixtures of diaryliodonium salts and/or triarylsulfonium salts can be used if desired. Exemplary diaryliodonium salts include diphenyliodonium salts, bis(4-t-butylphenyl)iodonium salts, bis(4-octylphenyl)iodonium salts, and bis(4-dodecylphenyl)iodonium salts. Diaryliodonium salts can be obtained commercially or synthesized by known methods. For example, many diaryliodonium salts are well-known and are described, for example, in U.S. Pat. Nos. 3,729,313 (Smith), 3,741,769 (Smith), 3,808,006 (Smith), 4,250,053 (Smith), and 4,394,403 (Smith), the diaryliodonium salt disclosures of which are incorporated herein by reference.

Exemplary triarylsulfonium salts and triarylsulfoxonium salts include triphenylsulfonium salts diphenyl(4-thiophenoxyphenyl)sulfonium salts, phenylditolylsulfonium salts, triphenylsulfonium salts, diphenyltolylsulfonium salts, phenylditolylsulfonium salts, and diphenylthiophenoxyphenylsulfonium salts, and those available from Sartomer Co., Exton, Pennsylvania, under the SARCAT trade designation, such as SARCAT CD 1010 [triarylsulfonium hexafluoroantimonate (50% in propylene carbonate)]; SARCAT DC 1011 [triarylsulfonium hexafluorophosphate (50% n-propylene carbonate)]; SARCAT DC 1012 (diaryliodonium hexafluoroantimonate); SARCAT K185 [triarylsulfonium hexafluorophosphate (50% in propylene carbonate)] and SARCAT SR1010 [triarylsulfonium hexafluoroantimonate (50% in propylene carbonate)]; and SARCAT SR1012 (diaryliodonium hexafluoroantimonate), and those available from Dow under the CYRACURE tradename, such as UVI-6976 mixture of triarylsulfonium hexafluoroantimonate salts in propylene carbonate. Triarylsulfonium slats and triarylsulfoxonium salts can be obtained commercially or synthesized by known methods.

Examples of suitable trihalomethyltriazines include 2,4,6-tris(trichloromethyl)-s-triazine and 2-alkyl-4,6-bis(trichloromethyl)-s-triazines, which can be obtained commercially or synthesized by known methods. In general, trihalomethyltriazines are useful in free-radically polymerizable compositions, but typically not in cationically polymerizable compositions.

In embodiments including five-radically polymerizable systems the photoinitiator system may further include an electron donor capable of transferring an electron into the photoexcited state of compounds according to Formula I. Suitable classes of electron donors may include dialkylaryl and tertiary alkylamines and tetraphenyl borates. Suitable electron donors may include tertiary amines often referred to in the context of radiation curing as amine synergists. Exemplary electron donors include 2-ethylhexyl 4-(dimethylamino)benzoate and 2-ethyl-(4-N,N-dimethylamino)benzoate, and tetraphenyl tetrafluoroborate, which fragments to generate a phenyl radical upon oxidation. Additional suitable electron donors include 10H-phenothiazine, phenoxazine, and 9,10-dihydro-9,9-dimethylacridine, and mono- and/or polyalkyl-substituted derivatives thereof, and combinations thereof. Still further electron donors include those represented by the Formula II, below:

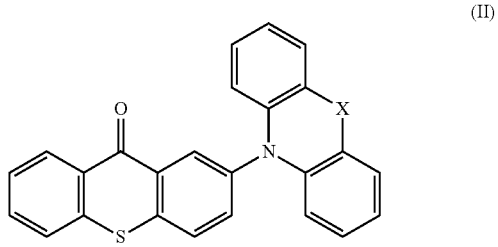

(II)

where X represents O, S, or —CR$^1_2$—, wherein R$^1$ is as previously defined.

Further details concerning electron donor and electron acceptors that are suitable for inclusion in to free-radically polymerizable compositions of the present disclosure can be found, for example, in U.S. Pat. No. 5,545,676 (Palazzotto et al.), the disclosure of which is incorporated herein by reference.

Electron donors can be obtained from commercial sources and/or synthesized according to known methods.

Polymerizable compositions according to the present disclosure polymerize on exposure to actinic electromagnetic radiation. While ultraviolet light may be used, polymerizable compositions according to the present disclosure may also be polymerized by exposure to certain visible light wavelengths (e.g., about 430 to about 450 nanometers (nm)). Suitable light sources include low, medium, and high pressure mercury lamps, xenon flashlamps, lasers, and Light Emitting Diodes (LEDs). Preferably free-radically polymerization is carried out in the substantial absence of oxygen, however this is not a requirement. Further details associated with radiation curing are with the capabilities of those skilled in the art.

Polymerization, whether complete or partial, results in a corresponding polymerized reaction product.

Polymerized reaction products according to the present disclosure may be useful, for example, as protective coatings and sealants.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight. Materials used in the examples are available from commercial suppliers and/or can be made by known methods, unless indicated otherwise. Materials prepared in the examples were analyzed by NMR spectroscopy and were consistent with the given structures.

TABLE 1

| MATERIAL | SOURCE |
| --- | --- |
| Carbazole | Oakwood Chemicals, Estill, South Carolina |
| 3,6-Di-tert-butylcarbazole | Oakwood Chemicals |
| 1,4-Dioxane (anhydrous) | MilliporeSigma, Saint Louis, Missouri |
| XPhos, 2-Dicyclohexylphosphino-2',4',6'-triisopropylbiphenyl | Strem Chemicals, Newbury Port, Massachusetts |
| XPhos Pd G3, 2-dicyclohexylphosphino-2',4',6'-triisopropyl-1,1'-biphenyl)[2-(2'-amino-1,1'-biphenyl)]palladium(II) methanesulfonate | MilliporeSigma |
| Pd$_2$(dba)$_3$, tris(dibenzylideneacetone)-dipalladium(0) | Strem Chemicals |
| 2-Chlorothioxanthone (CTX) | Alfa Aesar, Haverhill, Massachusetts |
| LiHMDS, lithium bis(trimethylsilyl)amide solution, 1.0M in THF | MilliporeSigma |
| ESCALOL 507, 2-ethylhexyl 4-(dimethylamino)benzoate | ISP VAN DYK, Inc., Belleville, New Jersey |
| OMNIRAD 819, bis(2,4,6-trimethylbenzoyl)phenylphosphine oxide | Ciba AG, Basel, Switzerland |
| IOD, bis(4-tert-butylphenyl)iodonium hexafluorophosphate | IGM Resins, St. Charles, Illinois |
| SR339, 2-phenoxyethyl acrylate | Sartomer, Exton, Pennsylvania |
| ITX, isopropyl-9H-thioxanthen-9-one, mixture of 2- and 4-isomers | Millipore Sigma |

TABLE 1-continued

| MATERIAL | SOURCE |
| --- | --- |
| CPTX, 1-chloro-4-propoxy-9H-thioxanthen-9-one | Millipore Sigma |
| CELLOXIDE 2021P, (3',4'-epoxycyclohexane)methyl 3,4-epoxycyclohexylcarboxylate | Daicel Chemical industries, Tokyo, Japan |
| CAPA 2054, polycaprolactone diol | Perstorp, Warrington, Cheshire, United Kingdom |

UV-VIS absorption properties of the compounds were recorded with a Cary 60 UV-VIS spectrometer (Agilent Technologies, Santa Clara, California).

Determination of Degree of Conversion (% Cure) Via FTIR:

Samples were placed between two glass slides, spaced with a hole-punched 30 mil rubber and fixed with binder clips. The degree of conversion was determined by monitoring the evolution of the (meth)acrylate or epoxy peak around 6160 and 3745 cm$^{-1}$, respectively. Data was collected with a Nicolet iS50 FTIR spectrometer.

Synthesis of 2-(9H-carbazol-9-yl)-9H-thioxanthen-9-one (CzTX)

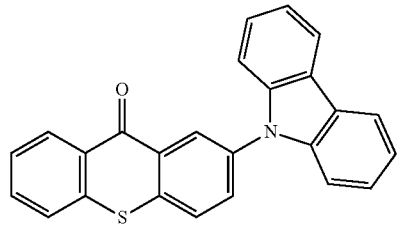 [SMILES: O=c1c2ccccc2sc2ccc(-n3c4ccccc4c4ccccc43)cc12]

In a flame-dried flask equipped with a reflux condenser under an atmosphere of argon, a mixture of 2-chlorothioxanthone (1.00 g, 4.05 mmol) carbazole (0.746 g, 4.46 mmol), Pd$_2$(dba)$_3$ (0.223 g, 0.243 mmol) and XPhos (0.290 g, 0,608 mmol) was dissolved in anhydrous 1,4-dioxane (40 mL). LiHMDS (4.90 mL, 4.90 mmol, 1.0 M in tetrahydrofuran (THF)) was added. After heating at 80° C. for 4 h, the solvent was removed from the reaction mixture in vacuo. The crude was dissolved in CH$_2$Cl$_2$ and subsequently washed with water and brine. The organic layer was dried over MgSO$_4$, filtered, and the solvent evaporated under reduced pressure. The product was obtained after purification using flash column chromatography (CH$_2$Cl$_2$/hexane gradient) as a yellow fluffy solid. UV-VIS spectral analysis indicated an absorption maximum at about 390 nanometers (ma) with a tail extending to about 440 nm.

Synthesis of 2-(3,6-di-tert-butyl-9H-carbazol-9-yl)-9H-thioxanthen-9-one (tBCzTX)

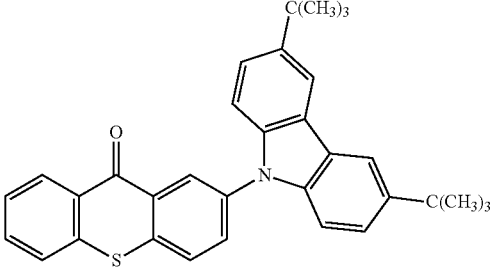 [SMILES: CC(C)(C)c1ccc2c(c1)c1cc(C(C)(C)C)ccc1n2-c1ccc2sc3ccccc3c(=O)c2c1]

In a flame-dried flask equipped with a reflux condenser under an atmosphere of argon, a mixture of 2-chlorothioxanthone (1.00 g, 4.05 mmol), 3,6-di-tert-butylcarbazole (1.25 g, 4.46 mmol) and XPhos Pd G3 (0.171 g, 0.202 mmol) was dissolved in anhydrous 1,4-dioxane (40 mL). LiHMDS (4.86 mL, 4.86 mmol, 1.0 M in THF) was added. After heating at 80° C. for 4 h, then at 100° C. for 3 hours, the solvent was removed from the reaction mixture in vacuo. The crude was dissolved in $CH_2Cl_2$ and subsequently washed with water and brine. The organic layer was dried over $MgSO_4$, filtered and the solvent evaporated under reduced pressure. The product was obtained after purification using flash column chromatography ($CH_2Cl_2$/Hexane gradient) as a yellow solid. UV-VIS spectral analysis indicated an absorption maximum at about 400 nm with a tail extending to about 450 nm.

In the following Examples, the blue light source was a 3M Paradigm DeepCure LED curing light, with an output of ~1,470 $mW/cm^2$ (450 nm).

Examples E-1 and E-2 and Comparative Example CE-A

The photoinitiator system (in amounts indicated in Table 2), N-methyl-2-pyrrolidone (0.5 parts), and SR339 (100 parts) were weighed out in a vial, heated and occasionally vortexed until fully solubilized. The formulation was placed in laminate (30 mils (0.76 mm) thickness) between glass slides. The samples were subsequently irradiated with the blue light source. Polymerization with high conversion was observed. A high degree of conversion was also demonstrated when the sample was cured at a distance of 2 inches (5.1 cm) distance from the blue light source. Results are reported in Table 2, below.

TABLE 2

| | PHOTOINITIATOR SYSTEM | | % CONVERSION | |
|---|---|---|---|---|
| | | | 20 sec exposure, 1 inch (2.5 cm) distance | 40 sec exposure, 2 inch (5.1 cm) distance |
| EXAMPLE | Component | Amount, parts | | |
| E-1 | CzTX | 0.5 | 95 | 95 |
| | IOD | 1.0 | | |
| CE-A | OMNIRAD 819 | 0.5 | 99 | 98 |
| E-2 | tBCzTX | 0.5 | 93 | 96 |
| | IOD | 1.0 | | |

Examples E-3 and E-4 and Comparative Example CE-B to CE-D

The photoinitiator system (in amounts indicated in Table 3) and SR339 (100 parts) were weighed out in a vial, heated and occasionally vortexed until fully solubilized. The formulation was placed in laminate (30 mils (0.76 mm) thickness) between glass slides. The samples were subsequently irradiated with the blue light source from a distance of one inch (2.54 cm) for 20 seconds. Results are reported in Table 3, below.

TABLE 3

| | PHOTOINITIATOR SYSTEM | | % CONVERSION 20 sec exposure, 1 inch (2.5 cm) distance |
|---|---|---|---|
| EXAMPLE | Component | Amount, parts | |
| E-3 | CzTX | 0.33 | 86 |
| | IOD | 1.0 | |
| E-4 | tBCzTX | 0.33 | 83 |
| | IOD | 1.0 | |
| CE-B | ITX | 0.33 | 47 |
| | IOD | 1.0 | |
| CE-C | CTX | 0.33 | <2 |
| | IOD | 1.0 | |
| CE-D | CPTX | 0.33 | <2 |
| | IOD | 1.0 | |

Examples E-5 and E-6 and Comparative Example CE-E and CE-F

The photoinitiator system (in amounts indicated in Table 4) and SR339 (100 parts) were weighed out in a vial, heated and occasionally vortexed until fully solubilized. The formulation was placed in laminate (30 mils (0.76 mm) thickness) between glass slides. The samples were subsequently irradiated with the blue light source from a distance of one inch (2.54 cm) for 20 seconds. Results are reported in Table 4, below.

TABLE 4

| | PHOTOINITIATOR SYSTEM | | % CONVERSION 20 sec exposure, 1 inch (2.5 cm) distance |
|---|---|---|---|
| EXAMPLE | Component | Amount, parts | |
| E-5 | CzTX | 0.33 | 93 |
| | ESCALOL 507 | 1.0 | |
| E-6 | tBCzTX | 0.33 | 94 |
| | ESCALOL 507 | 1.0 | |
| CE-E | CPQ | 0.33 | 94 |
| | ESCALOL 507 | 1.0 | |
| CE-F | CPTX | 0.33 | 88 |
| | ESCALOL 507 | 1.0 | |

Examples E-7 and E-8

The photoinitiator system (in amounts indicated in Table 5), CAPA 2054 (25 parts), and CELLOXIDE 2021P (75 parts) were weighed out in a vial, heated and occasionally vortexed until fully solubilized. The formulation was placed in laminate (30 mils (0.76 mm) thickness) between glass slides. The samples were subsequently irradiated with the blue light source from a distance of one inch (2.54 cm) for 20 seconds. Results are reported in Table 5, below.

TABLE 5

| | PHOTOINITIATOR SYSTEM | | % CONVERSION 20 sec exposure, 1 inch (2.5 cm) distance |
|---|---|---|---|
| EXAMPLE | Component | Amount, parts | |
| E-7 | CzTX | 0.33 | 31 |
| | IOD | 1.0 | |
| E-8 | tBCzTX | 0.33 | 28 |
| | IOD | 1.0 | |

Examples E-9 and E-10

The photoinitiator system (0.33 parts) and SR339 (100 parts) were weighed out in a vial, heated and occasionally vortexed until fully solubilized. The formulation was placed in laminate (30 mils (0.76 mm) thickness) between glass slides. The samples were subsequently irradiated with the blue light source from a distance of one inch (2.54 cm) for 20 seconds. Results are reported in Table 6, below.

TABLE 6

| EXAMPLE | PHOTOINITIATOR SYSTEM | % CONVERSION, 20 sec exposure, 1 inch (2.5 cm) distance |
|---|---|---|
| E-9 | CzTX | 20 |
| E-10 | tBCzTX | 25 |

All cited references, patents, and patent applications in this application that are incorporated by reference, are incorporated in a consistent manner. In the event of inconsistencies or contradictions between portions of the incorporated references and this application, the information in this application shall control. The preceding description, given in order to enable one of ordinary skill in the art to practice the claimed disclosure, is not to be construed as limiting the scope of the disclosure, which is defined by the claims and all equivalents thereto.

What is claimed is:

1. A polymerizable composition comprising:
   at least one free-radically polymerizable compound; and
   a photoinitiator system, wherein the photoinitiator system comprises a compound represented by the formula:

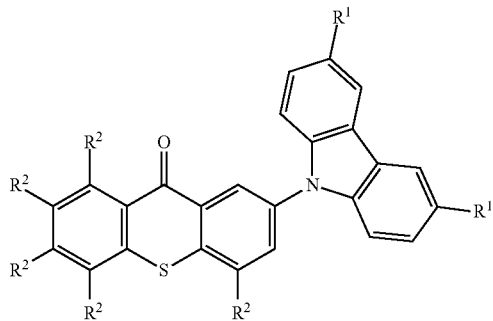

wherein:
   each $R^1$ independently represents or an alkyl group having from 1 to 6 carbon atoms, and
   four $R^2$ are H and one $R^2$ represents H, an alkyl group having from 1 to 4 carbon atoms, an alkoxy group having from 1 to 4 carbon atoms, F, Cl, or Br.

2. The polymerizable composition of claim 1, wherein the photoinitiator system further comprises a diaryliodonium compound.

3. The polymerizable composition of claim 1, wherein the photoinitiator system further comprises a tertiary dialkylarylamine.

4. The polymerizable composition of claim 1, wherein the at least one free-radically polymerizable compound comprises at least one (meth)acrylate monomer.

5. The polymerizable composition of claim 1, wherein the at least one free-radically polymerizable compound comprises at least one N-vinylamide.

6. The polymerizable composition of claim 1, wherein each $R^1$ is a tertiary butyl group.

7. The polymerizable composition of claim 1, wherein each $R^2$ is H.

8. A polymerized reaction product of the polymerizable composition of claim 1.

9. A polymerizable composition comprising:
   at least one cationically polymerizable compound;
   a diaryliodonium salt; and
   a photoinitiator system, wherein the photoinitiator system comprises a compound represented by the formula:

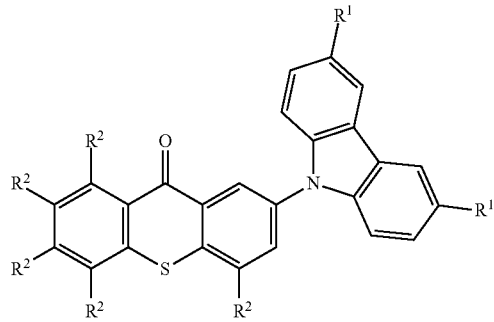

wherein:
   each $R^1$ independently represents an alkyl group having from 1 to 6 carbon atoms, and
   four $R^2$ are H and one $R^2$ represents H, an alkyl group having from 1 to 4 carbon atoms, an alkoxy group having from 1 to 4 carbon atoms, F, Cl, or Br.

10. The polymerizable composition of claim 9, wherein the at least one cationically polymerizable compound comprises at least one of an epoxy resin or a vinyl ether.

11. The polymerizable composition of claim 9, wherein each $R^2$ is H.

12. A polymerized reaction product of the polymerizable composition of claim 9.

* * * * *